US010502691B1

(12) United States Patent
Packard et al.

(10) Patent No.: US 10,502,691 B1
(45) Date of Patent: Dec. 10, 2019

(54) SYSTEMS AND METHODS FOR INSPECTION AND DEFECT DETECTION

(71) Applicant: CaaStle, Inc., New York, NY (US)

(72) Inventors: Alyssa Packard, Asheville, OH (US); Shannon Gramley, Columbus, OH (US); Lindsey Winland, Dublin, OH (US)

(73) Assignee: CAASTLE, INC., New York, NY (US)

( * ) Notice: Subject to any disclaimer, the term of this patent is extended or adjusted under 35 U.S.C. 154(b) by 0 days.

(21) Appl. No.: 16/370,297

(22) Filed: Mar. 29, 2019

(51) Int. Cl.
*G01N 21/88* (2006.01)
*G01N 21/93* (2006.01)

(52) U.S. Cl.
CPC ......... *G01N 21/93* (2013.01); *G01N 21/8803* (2013.01)

(58) Field of Classification Search
CPC combination set(s) only.
See application file for complete search history.

(56) References Cited

U.S. PATENT DOCUMENTS

| 4,974,261 | A | * | 11/1990 | Nakahara | G01N 21/88 348/128 |
|---|---|---|---|---|---|
| 5,586,058 | A | * | 12/1996 | Aloni | G01N 21/956 07 382/141 |
| 5,774,177 | A | * | 6/1998 | Lane | D06H 3/08 348/128 |
| 5,943,125 | A | * | 8/1999 | King | G01N 21/956 84 356/237.1 |
| 6,075,880 | A | * | 6/2000 | Kollhof | G01N 21/8851 382/141 |
| 6,115,490 | A | * | 9/2000 | Platsch | B41F 23/06 250/559.46 |
| 6,178,262 | B1 | * | 1/2001 | Picard | G06K 9/4604 382/195 |
| 6,266,138 | B1 | * | 7/2001 | Keshavmurthy | G01B 11/303 356/237.2 |
| 6,452,671 | B1 | * | 9/2002 | Uda | G01N 21/956 356/237.2 |
| 6,452,686 | B1 | * | 9/2002 | Svetkoff | G01B 11/026 250/201.3 |
| 6,630,996 | B2 | * | 10/2003 | Rao | G01N 21/9501 356/237.1 |
| 7,826,047 | B2 | * | 11/2010 | Shibata | G01N 21/8806 356/237.2 |
| 7,843,558 | B2 | * | 11/2010 | Furman | G01N 21/8806 356/237.1 |
| 9,726,617 | B2 | * | 8/2017 | Kolchin | H05K 999/99 |
| 2002/0181760 | A1 | * | 12/2002 | Asai | G01N 21/95692 382/149 |

(Continued)

FOREIGN PATENT DOCUMENTS

EP 0610956 A2 * 8/1994 .......... G01N 21/909

*Primary Examiner* — Mohamed K Amara
(74) *Attorney, Agent, or Firm* — Bookoff McAndrews, PLLC

(57) ABSTRACT

A method of inspecting an article with a defect detection tool includes receiving one or more articles at an inspection station and inspecting one of the received one or more articles at the inspection station by evaluating the article for at least one physical defect with the defect detection tool. The defect detection tool includes a clear body including a surface element sized to correspond to the at least one physical defect in the article, and an inspection surface configured to contact a surface of the article.

17 Claims, 7 Drawing Sheets

(56) References Cited

U.S. PATENT DOCUMENTS

| | | | | |
|---|---|---|---|---|
| 2002/0186368 | A1* | 12/2002 | Rosengaus | G01N 21/9501 356/237.2 |
| 2003/0179920 | A1* | 9/2003 | Hooker | G06T 7/001 382/141 |
| 2004/0207836 | A1* | 10/2004 | Chhibber | G01N 21/4738 356/237.4 |
| 2005/0036135 | A1* | 2/2005 | Earthman | G01N 21/4738 356/237.1 |
| 2005/0094136 | A1* | 5/2005 | Xu | G01N 21/21 356/237.3 |
| 2006/0091333 | A1* | 5/2006 | Cochran | G01N 21/8806 250/559.16 |
| 2006/0181700 | A1* | 8/2006 | Andrews | G01N 21/21 356/237.2 |
| 2006/0199287 | A1* | 9/2006 | Fu | G01N 21/9501 438/16 |
| 2008/0040064 | A1* | 2/2008 | Ishikawa | G01N 21/9501 702/108 |
| 2009/0254209 | A1* | 10/2009 | Tan | G01N 21/8851 700/110 |
| 2010/0004875 | A1* | 1/2010 | Urano | G01N 21/4738 702/40 |
| 2010/0118136 | A1* | 5/2010 | Riet | G01B 11/306 348/92 |
| 2013/0177232 | A1* | 7/2013 | Hirano | G06T 7/0004 382/141 |
| 2015/0116712 | A1* | 4/2015 | Otani | G01N 21/21 356/364 |
| 2017/0315062 | A1* | 11/2017 | Matsuda | G01N 21/8806 |
| 2018/0122060 | A1* | 5/2018 | Shirkhodaie | G06T 7/0008 |
| 2018/0322623 | A1* | 11/2018 | Memo | G06N 3/084 |

\* cited by examiner

SYSTEMS AND METHODS FOR INSPECTION AND DEFECT DETECTION

TECHNICAL FIELD

The present disclosure relates generally to the field of processing and inspecting an article for an end user and, more particularly, to systems and methods for inspecting and detecting defects in articles.

BACKGROUND

The clothing and fashion industry has traditionally depended on a business model where customers purchase goods from physical retail locations. These goods are often discarded by the customer while the item remains in good condition or even excellent condition. Numerous retail locations are necessary to attract customers and provide sufficient space for the display of items and to stock items of different styles, sizes, etc. These physical retail locations are operated by teams of employees and are both labor-intensive and expensive to maintain. Additionally, each physical location can only attract consumers within a narrow geographic area. It is also expensive and difficult to adapt multiple retail locations to rapidly-changing trends.

Although many industries have successfully migrated to Internet-connected platforms, the clothing industry largely remains dependent on physical retail stores and traditional business models. Even when a sale of clothing is performed over the Internet, the item may still be used infrequently by a single consumer before being discarded. Thus, the fashion and clothing industry also produces a significant amount of waste. Accordingly, there is a need to transition to more efficient practices.

Various challenges face retailers seeking to transition to alternate strategies that provide items for short-term or temporary use. One such challenge lies in inspecting inbound articles that are received from a customer or from a supplier. Current rental services do not typically perform a detailed inspection on articles that are received by customers. Rather, these rental services rely upon customers to detect and report items that are damaged or otherwise unsatisfactory. This can result in various problems, including inaccurate tracking of item condition, inaccurate reporting of items as damaged, and inconsistent reporting standards. Additionally, relying upon customers to report damaged or unsatisfactory items can result in a poor customer experience, as the customer receiving the unsatisfactory item must take action to report the item and wait for replacement of the item.

Additional challenges face retailers seeking to transition to alternate strategies that provide items for short-term or temporary use, especially when the items may require frequent inspection for quality. One such challenge lies in managing inbound articles for inspection, performing the inspection in an objective and controllable manner, and accumulating useful data based on the result of each inspection. Present systems are not equipped to provide objective inspection standards, particularly when items are inspected in multiple categories, or when the items are inspected in different areas with differing inspection standards.

There is a need for systems and methods to provide a repeatable, objective standard for inspecting an article, and to record the result of the inspection in an accurate and repeatable manner. Such needs are particularly felt when articles include multiple inspection areas and the articles differ from each other. Thus, the present disclosure is directed to inspecting an article, more particularly, to systems and methods for detecting defects in articles.

SUMMARY

In one aspect, a method of inspecting an article with a defect detection tool may include receiving one or more articles at an inspection station and inspecting one of the received one or more articles at the inspection station by evaluating the article for at least one physical defect with the defect detection tool. The defect detection tool may include a clear body including a surface element sized to correspond to the at least one physical defect in the article, the surface element including at least one of a linear element or a circular element and an inspection surface configured to contact a surface of the article when the clear body is applied to the article. Evaluating the article for at least one physical defect with the defect detection tool may include applying the defect detection tool against the article to align the surface element with a potential physical defect in the surface of the article and determining that the at least one physical defect is present when the potential physical defect has a size equal to or larger than a size of the linear element or a size of the circular element.

In another aspect, a computer-implemented method of detecting a defect in an article may include receiving one or more articles at an inspection station, and inspecting the article using a defect inspection tool having a surface element to indicate a presence of a physical defect in the article. The inspecting may include determining a standard for inspecting an area of the article with the defect inspection tool, evaluating the article for at least one physical defect based on the determined standard, based on the evaluation, determining whether the article includes the at least one physical defect, and when the article is determined to include the at least one physical defect, updating an article tracking system with an inspection processor.

In another aspect, an inspection defect detection tool for detecting at least one physical defect in an article may include a clear body having a surface element sized to correspond to the at least one physical defect in the article, the surface element including at least one of a linear element or a circular element, the circular element formed as a depression, a through-hole, or a portion of the inspection surface having a color different than the clear body. The inspection defect detection tool may also include an inspection surface formed on the clear body, the inspection surface configured to contact a surface of the article when the clear body is applied to the article such that the surface element is approximately aligned with a potential physical defect in the article.

BRIEF DESCRIPTION OF THE DRAWINGS

It is believed that certain embodiments will be better understood from the following description taken in conjunction with the accompanying drawings, in which like references indicate similar elements and in which.

DETAILED DESCRIPTION OF EMBODIMENTS

While principles of the present disclosure are described herein with reference to illustrative embodiments for particular applications, it should be understood that the disclosure is not limited thereto. Those having ordinary skill in the art and access to the teachings provided herein, will recognize that the features illustrated or described with respect to one embodiment, may be combined with the features of another embodiment. Therefore, additional modifications, applications, embodiments, and substitution of equivalents, all fall within the scope of the embodiments described herein. Accordingly, the invention is not to be considered as limited by the foregoing description. Various non-limiting embodiments of the present disclosure will now be described to provide an overall understanding of the principles of the structure, function, and use of system and method for article inventory transfer.

As described above, there is a need in the field of processing an article for an end user. In one aspect, processing an item for an end user may include the performance of a service of providing articles to end users.

Figure 1:
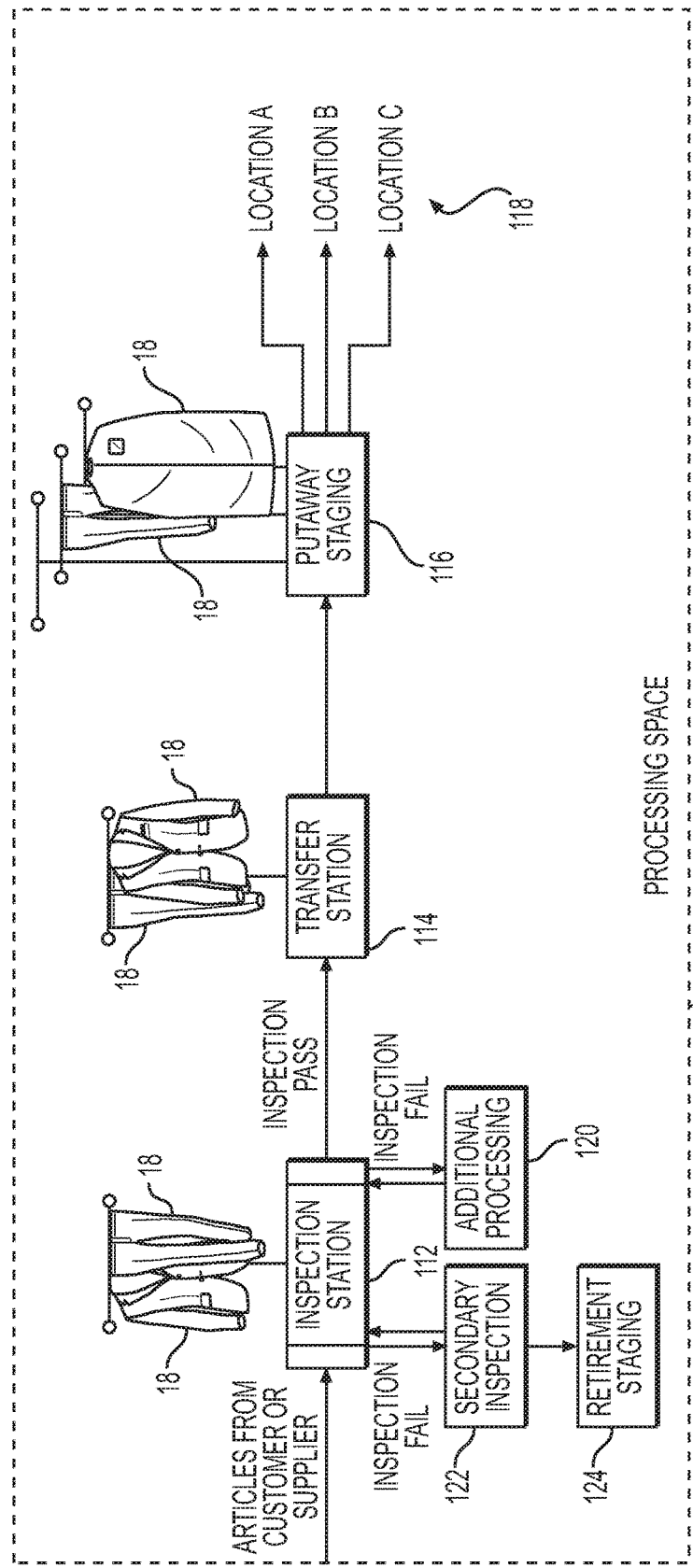
FIG. 1 is a schematic diagram of a workflow applicable to a service of providing articles including an inspection system according to an embodiment of the present disclosure.

FIG. 1 illustrates an exemplary workflow that may be applied to a service of providing articles to end users (e.g., clothing as a service). The articles are, for example, wearable articles such as garments and/or accessories that are provided as a service to numerous users. As shown in FIG. 1, one or more articles 18 are received in a processing space 110 before being transferred to one or more destination locations 118 within the processing space 110. Processing space 110 may be, for example, an interior of a warehouse in which a number of articles 18 are received, cleaned, inspected, repaired, stored, and/or prepared for shipment to users. Each article 18 may be a new article received from a supplier (new arrival) or an article that was worn by a customer.

As shown in FIG. 1, in general, processing space 110 may comprise an inspection station 112, a transfer station 114, a putaway staging area 116, a retirement staging area 124, an additional processing area 120, a secondary inspection station 122, and a plurality of destination locations 118. Destination locations 118 may be locations within a single processing space 110 or within multiple processing spaces 110. Similarly, while inspection station 112, transfer station 114, and putaway staging area 116 may each be located within a single processing space 110, one or more of these may be located in various warehouses or processing spaces 110. While one inspection station is illustrated in FIG. 1, a plurality of inspection stations 112 may be provided within processing space 110 to increase productivity. Similarly, multiple transfer stations 114 and putaway staging areas 116 may be provided, and may be present in more or fewer locations than inspection stations 112.

One or more articles 18 may be received in the processing space 110 to be transferred to one or more destination locations 118 within the processing space 110. Prior to being transferred to destination locations 118, each article 18 may be individually inspected at an inspection station 112. An inspection at inspection station 112 may include evaluating article 18 for at least one quality criterion such as the presence of a stain, color bleeding, tearing, snagging, broken stitching, odor, dirt, wrinkling, shrinkage, wear, pilling, color fading, missing or broken hardware, or missing or broken embellishments.

Depending on the result of the inspection performed at inspection station 112, the article 18 may be transferred to an additional processing area 120, secondary inspection station 122, a retirement staging area 124, or a transfer station 114. As can be seen in FIG. 1, articles 18 that pass inspection are relocated from inspection station 112 to a transfer station 114. From the transfer station 114, each article 18 may be subsequently transferred to putaway staging area 116. From putaway staging area 116, groups of articles 18 may be transferred to destination locations 118.

Figure 2:
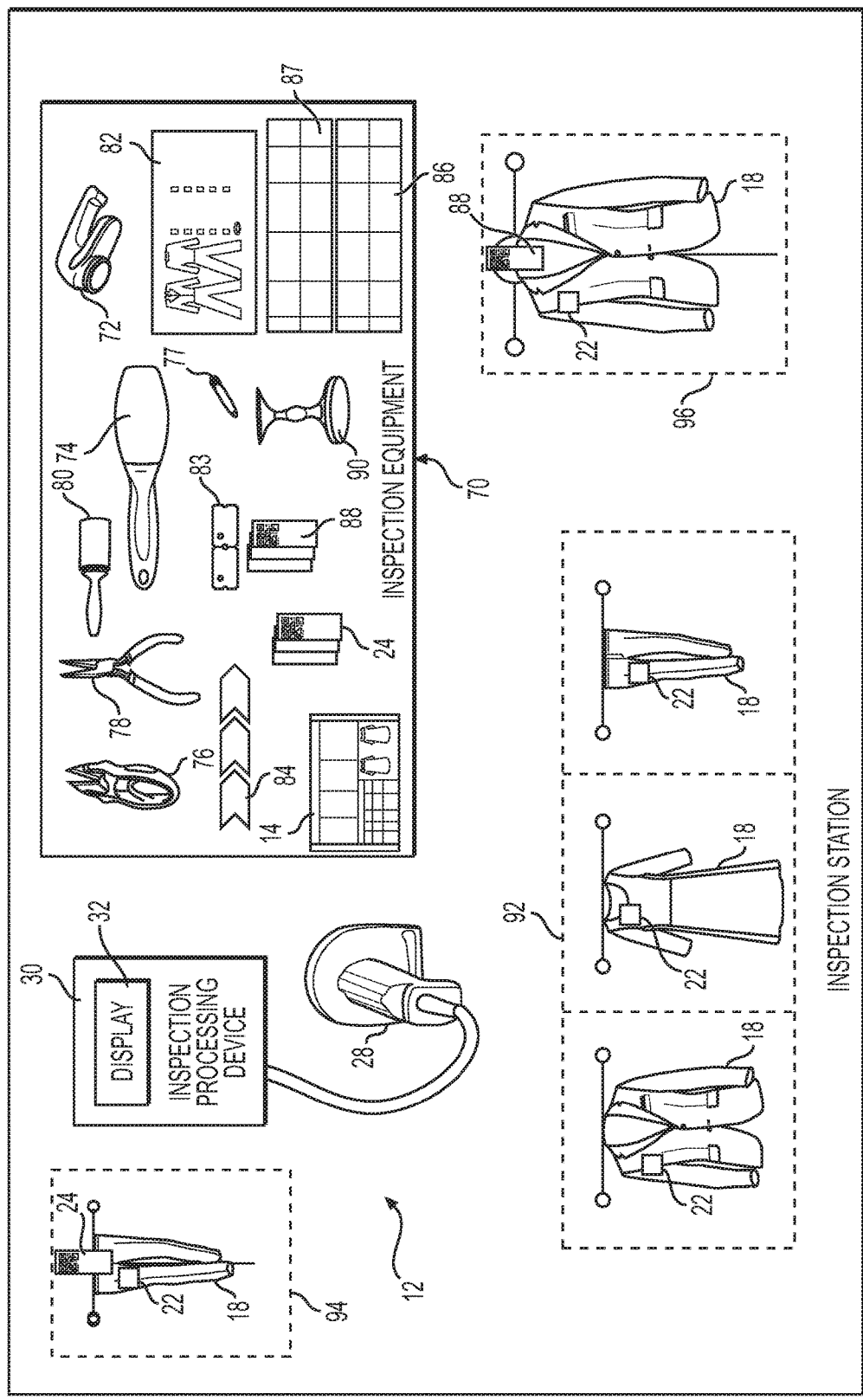
FIG. 2 is block diagram illustrating an inspection system including an inspection station, according to an embodiment of the present disclosure.

FIG. 2 is a block diagram illustrating an exemplary inspection station 112 within processing space 110. Inspection station 112 includes space(s) to organize articles 18 before or after inspection and includes equipment 70 necessary to perform inspection and minor repairs. An inspection system 12 may be provided within inspection station 112 to assist in the inspection and tracking of articles 18. Inspection system 12 may include, for example, article identifiers 22, inspector identifiers 24, an inspection processor or inspection processing device 30, a reader 28 that is capable of reading identifiers 22 and 24, and inspection equipment 70. Inspection system 112 may include a series of lanes 92, 94, and 96, for managing a flow of articles 18 in a controlled manner.

Articles 18 within a first lane 92 may be organized on one or more racks (e.g., Z-racks) to await inspection. Articles 18 in first lane 92 may be new arrivals received from a supplier, received from a customer (after being laundered), or a mix of the two. A second lane 94 may be provided for articles 18 that passed inspection. Third lane 96 may include one or more racks of articles 18 that failed inspection. Racks within third lane 96 may have dividers corresponding to a destination, such as a repair station, retirement staging area 124, a cleaning station, a spotting station, or a pressing/steaming station. In one aspect, fail plates 88 (FIG. 2) may be used as dividers for articles in lane 96. Each fail plate may correspond to a particular destination associated with a cause of failure. During inspection, an inspector gathers an item from a rack in first lane 92, performs an inspection using inspection system 12, and transfers the article to second lane 94 or third lane 96 based on the result of the inspection.

Inspection system 12 may include identifiers 22 and an inspection processing device 30 that is configured to read the article identifiers 22 with reader 28. Inspection processing device 30 may include a computer that is operatively connected to reader 28. Inspection processing device 30 may include a display 32. Display 32 may be an input/output (I/O) device including a touchscreen.

Each identifier 22 may represent (encode) various types of information that is deciphered by inspection processing device 30. For example, each identifier 22 may encode a source (e.g., brand, manufacturer), category (e.g., dress, pants, top, etc.), style (e.g., summer, fall, beachwear, etc.), color, size, and/or serial number (e.g., one or more numbers or letters that uniquely identify identical articles 18). Reader 28 may be a hand-held device configured to read identifiers 22, 24, and 26. For example, each of identifiers 22, 24, and 26 may be formed as a tag. As used herein a "tag" refers to at least one of a one-dimensional barcode, a two-dimensional barcode (e.g., a quick-response or "QR" code, FIG. 3), or a radio-frequency identifier such as an RFID tag, any of which may be read by reader 28. Alternatively, reader 28 may be affixed to or incorporated within inspection processing device 30. As used herein, "reading" contemplates at least one of scanning (e.g., by a detector that detects reflected light such as a laser), imaging (e.g., by a camera of a cellular phone), infrared communication, or radio-frequency communication. In one aspect, reader 28 may include a camera or other imaging device configured to image a one-dimensional or two-dimensional barcode. Reader 28 is able to output information corresponding to each unique article identifier 22 by reading or scanning identifier 22.

Figure 3:
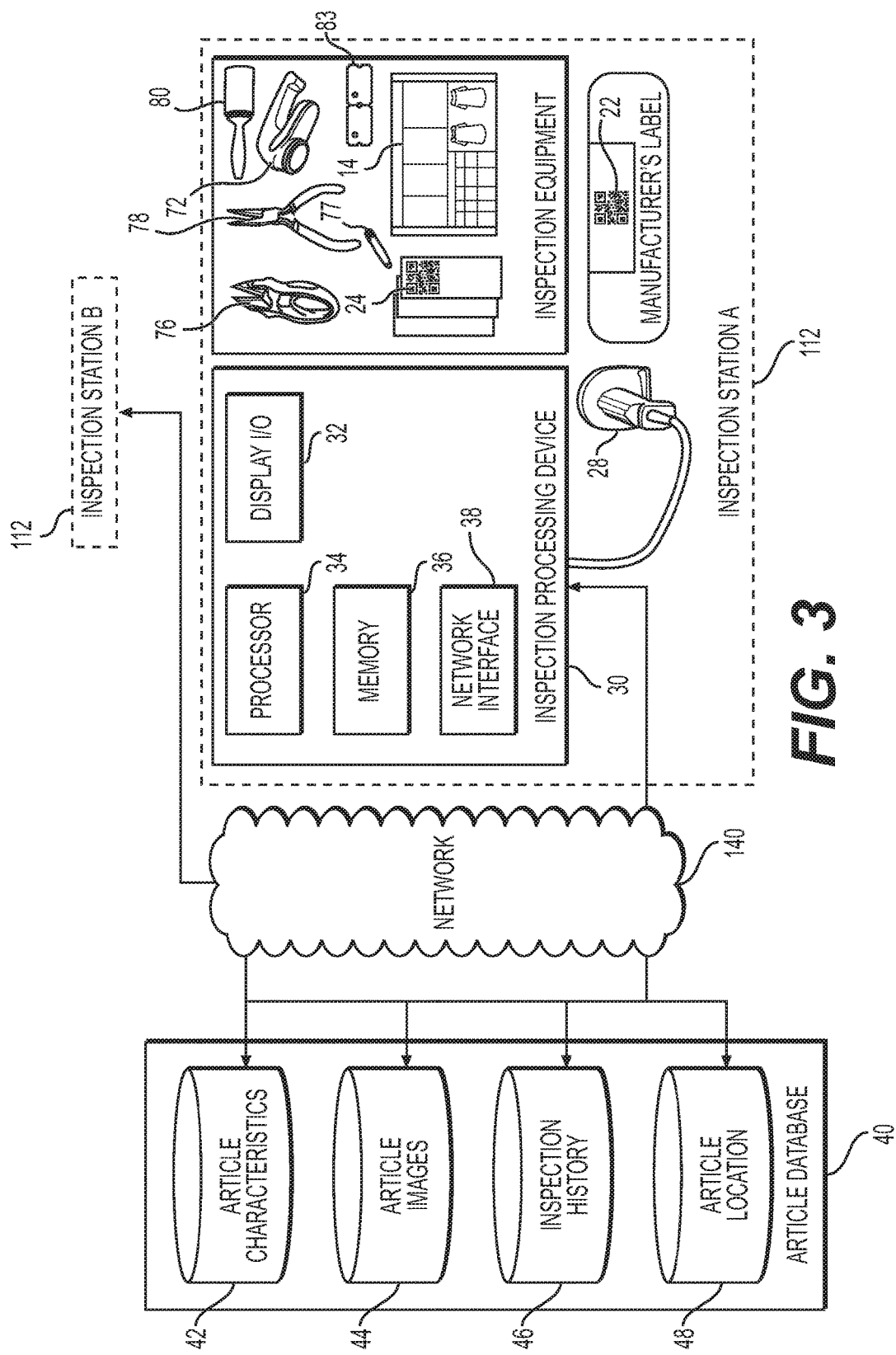
FIG. 3 is a block diagram illustrating an electronic network and environment including the inspection system of FIG. 2.

For ease of use, each identifier 22 may be physically attached to an interior of the corresponding article 18 (e.g., by fastening identifier 22 to an inside of a manufacturer's tag as shown in FIG. 3, or to a pocket on an interior of article 18). Thus, identifier 22 may remain fixed to article 18 during the life of the article 18, including when article 18 is worn by a customer, transported, laundered, etc. To ease understanding, identifier 22 is enlarged in FIG. 2. However, as shown in FIG. 3, identifier 22 may be provided in a size approximately the same as, or smaller than, a manufacturer's branding or care label provided on article 18.

As noted above, inspection equipment 70 may be included within an inspection station 112 to facilitate the inspection of articles 18 and perform minor care or repairs during the inspection. Inspection equipment 70 may include inspector identifiers 24 that associate one or more articles 18 with a particular inspector that performed the inspection. Each inspector identifier 24 may include a tag or code that corresponds to the particular inspector.

Inspection equipment 70 may include a defect detection tool or inspection tool 14 that may be used by an inspector during an inspection process. In one aspect, a plurality of inspection tools 14 may be included in the inspection equipment 70. When a plurality of inspection tools 14 are provided, these inspection tools 14 may be identical to each other. However, if desired, a plurality of different types of inspection tools 14 may be provided to facilitate the inspection of various articles 18. For example, a plurality of different types of inspection tools 14 may include inspection tools for shirts and different inspection tools for pants.

Inspection equipment 70 may also include a shaving device 72, lint brush 74, cutting tool 76, one or more safety pins 77, pliers 78, lint roller 80, action tags 82, multiple fail identifiers 83, spot stickers 84, production worksheet 86, first-in first-out (FIFO) sheet 87, fail plates 88, and cashmere brush 90. Thus, an inspector may correct minor imperfections and identify articles 18 that failed inspection. Multiple fail identifiers 83 may be provided as tags, for example, which are employed to identify an article 18 which failed an inspection for more than one inspection criterion. For example, an article 18 that failed for a reparable seam tear and a removable stain may be identified by affixing a multiple fail identifier 83 and an action tag 82 to the article 18. One or more production worksheet 86 and FIFO sheet 87 may be used to record an inspectors' productivity and ensure that each article 18 or rack of articles 18 is processed in order of arrival.

FIG. 3 is a block diagram illustrating an environment including an article tracking system or database 40 that may be used with inspection processing devices 30 in one or more inspection stations 112 (e.g., inspection station A and inspection station B). Article database 40 may be operatively connected, for example over network 140, with one or more inspection processing devices 30. In one aspect, network 140 may represent the Internet. However, network 140 may be a wired or wireless local network, or an intranet. Information stored in article database 40 is accessible by inspection processing device 30 via network 140, and may be added to, modified, or deleted by inspection processing device 30.

As discussed above, inspection processing device 30 may include a computer. A memory 36 of processing device 30 may store instructions that, when executed by one or more processors 34, allow processing device 30 to operate as discussed herein. While display I/O or display 32 may be a touchscreen display, additional I/O devices such as a mouse or keyboard may also be included in display I/O 32. Inspection processing device 30 may include a wired or wireless network interface 38 configured to access article database 40 through a network 140.

Article tracking system or article database 40 may include one or more storage devices that store article information. Each storage device may be formed by one or more hard disk drives, solid state drives, flash memory, USB storage devices, or other non-transitory storage media. Article database 40 may include an article characteristics storage device 42, article images storage device 44, inspection history storage device 46, and article location storage device 48. Although each storage device is illustrated as a part of database 40, one or more storage device may be combined and shared across one or more additional databases. Thus, when inspection stations 112 are located in processing spaces 110 of multiple warehouses, all of the information contained in article database 40 is readily accessed by each inspection processing device 30.

Whether article database 40 is connected to inspection processing device 30 by a global or local network 140, each inspection processing device 30 may access information stored in article characteristics storage 42, article images storage 44, inspection history storage 46, and article location storage 48. When reader 28 reads an identifier 22, information encoded in the identifier is output by reader 28 and received by processing device 30. This information may form the basis of a query sent from processing device 30 to article database 40. In response to the query, article database 40 outputs, via network 140, information from one or more of the categories of information associated with the identifier 22 that was read by reader 28. Thus, each article 18 may be identified in response to reading an identifier 22 by reader 28.

The information output from article database 40 may include article characteristics stored in storage 42. This information may include a source, category, style, color, size, etc. Article images storage 44 may include a photograph or stock image of the article 18. This image may represent an initial state of the article 18 when the article 18 is in new condition.

Inspection history storage 46 may include a complete history for every inspection performed on each article 18. The history may be stored in a generalized form (e.g., general pass/fail information) or may be more granular. For example, the inspection history stored in storage 46 may include both broader categories of failure (e.g., re-clean, odor, spotting, re-press, repair, retire, etc.) and detailed causes of failure (e.g., tear/hole located away from seam, color bleed, pilling, snagging, shrinkage, spandex wear). A detailed cause of failure stored in storage 46 may be updated based on an inspection of an article 18 performed with inspection tool 14.

Location information of each article 18 may be stored in article location storage 48. This location information may specify a location of the article 18 within a particular processing space 110, a particular location within processing space 110 (e.g., awaiting an audit or second inspection at secondary inspection station 122), or may indicate that the article 18 is with a customer (e.g., by storing a unique user identification number associated with the customer).

Information stored by article database 40 may be updated by processing device 30 in response to the output of reader 28. For example, processing device 30 may update article location information of an article 18 in response to being read by reader 28, or in response to an outcome of an inspection. In one aspect, inspection history information in storage 46 may be updated based on an outcome of an inspection performed at inspection station 112. Inspection processing device 30 may determine the result of an inspection by guiding an inspector through a series of prompts and receiving an inspection result from reader 28 or other input device. The result of the inspection may then be used to update the inspection history information, article location information, and any other relevant information stored by article database 40. Additionally, the inspection history can be updated based on the identifier 22 read by reader 28 to ensure that the inspection result is correlated with the correct article 18. Thus, inspection processing device 30 and inspection tool 14 may be used in conjunction in inspection system 12 to perform an objective inspection of articles 18 and record the results of the inspection accordingly.

Figure 4:
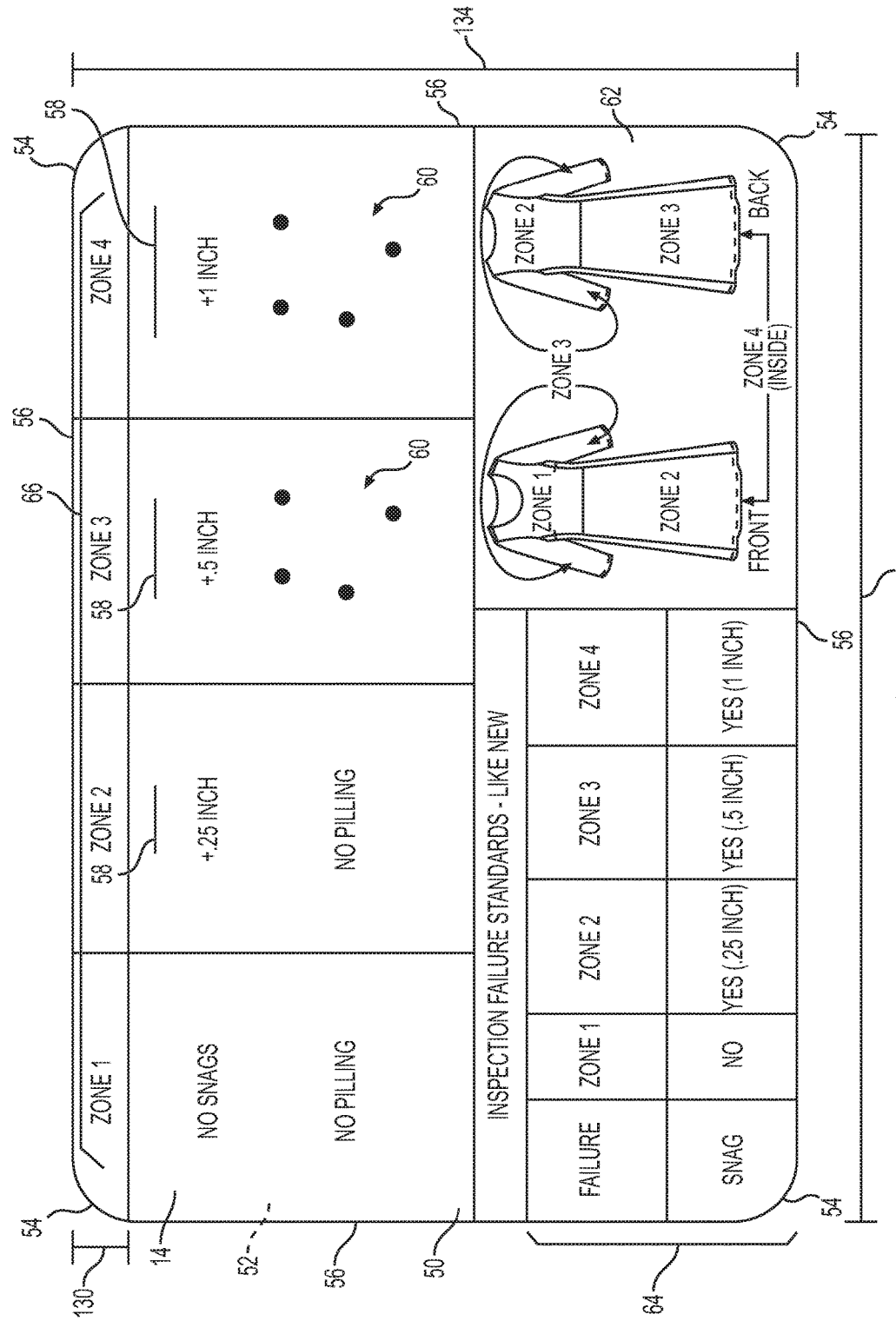
FIG. 4 is a plan view of a defect detection tool according to an embodiment of the present disclosure.

FIG. 4 is a plan view illustrating inspection tool 14 according to an exemplary embodiment. In one aspect, inspection tool 14 may be formed as an integrated tool having a clear or approximately clear body 50. Body 50 may define an inspection surface 52, rounded corners 54, and curved side edges 56. In one aspect, corners 54 and curved side edges 56 may include curved (e.g., rounded) boundaries on a bottom surface of body 50, the curved or rounded boundaries facing a surface of article 18 underneath tool 14. These boundaries may form a substantially smooth surface that prevents snagging of article 18, even when tool 14 is guided along a surface of the article 18. Additionally, each surface of tool 14 may be provided with a clear scratch-resistant coating. If desired, a clear scratch-resistant coating may be applied only to surfaces that may come into contact with an article 18, such as inspection surface 52.

Body 50 may include one or more linear surface features or elements 58 and/or one or more circular surface features or elements 60. A portion of body 50 may include an area division indicator 62 configured to indicate a plurality of different inspection areas of an article 18. An inspection standard indicator 64 may indicate one or more inspection standards for a plurality of areas in article 18. An inspection area specifier or area indicator 66 may be provided at another portion of body 50, such as an upper portion.

An inspection surface 52 of body 50 may be formed by a smooth surface body 50 that may be placed on an article 18 so as to align a potential physical defect in an article 18 with surface elements 58, 60. In an exemplary configuration, inspection surface 52 is formed by an approximately flat bottom surface of body 50.

Figure 5:
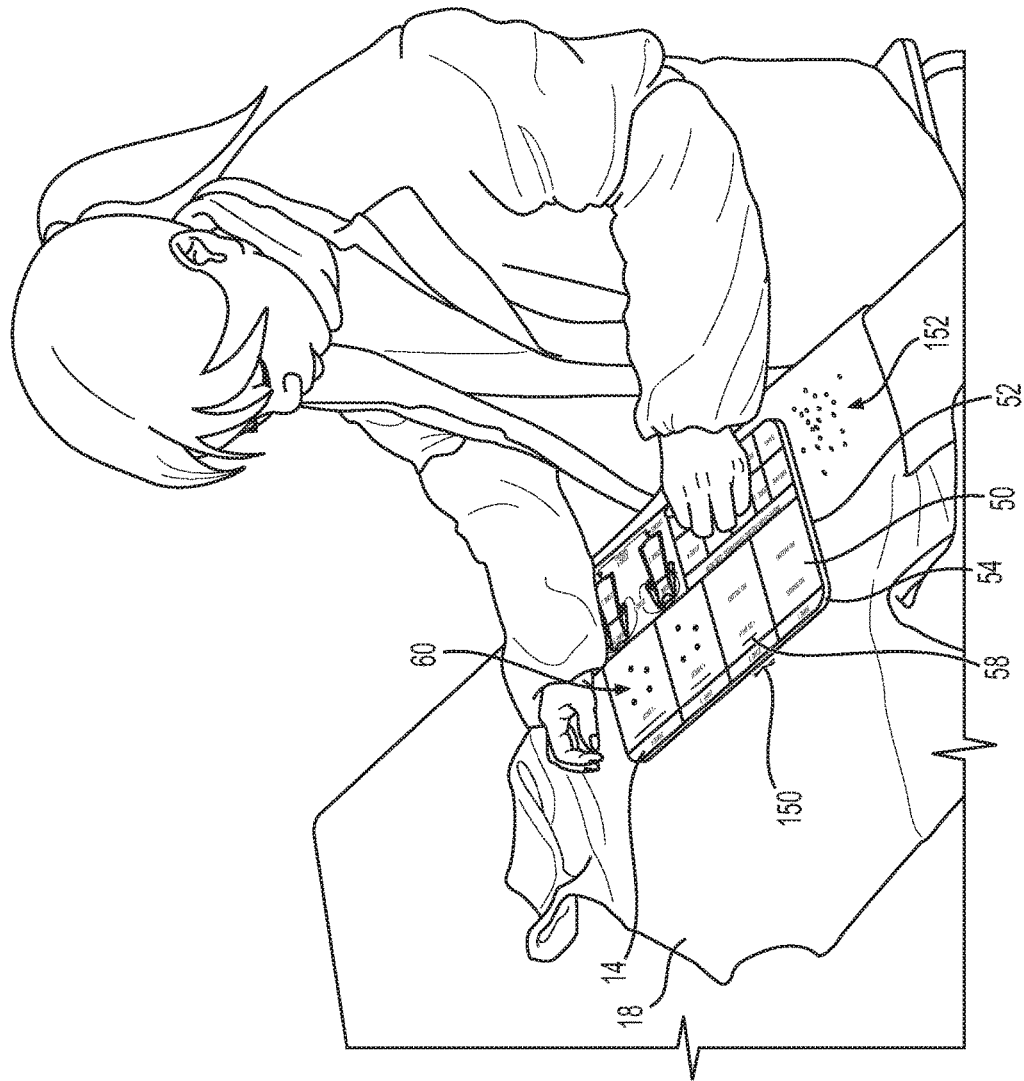
FIG. 5 is a perspective view showing an inspection performed with the defect detection tool of FIG. 4.

One or more of the surface elements 58 and 60 may be provided on an exterior surface of body 50, such as inspection surface 52, which may be a bottom surface of body 50 (FIG. 5). Alternatively, surface element 58 and/or surface element 60 may be provided on an upper surface of body 50 opposite to inspection surface 52. In another exemplary configuration, surface elements 58 and/or 60 may be provided in an interior surface of (e.g., embedded within) body 50. This may be performed, for example, by providing a layer of body 50 that has one or more portions formed of a different color than the remainder of clear body 50.

In one example, surface elements in body 50 may be formed by one or more linear surface features or linear elements 58. Linear element 58 may be formed as a depression, a through-hole, or a portion of body 50 such as surface 52 having a color different than the clear body 50. In an exemplary configuration, linear element 58 may be formed as a shallow groove or recess within body 50. As body 50 may be formed of a transparent (clear) material, a shallow groove or recess may provide a linear element 58 that is translucent. Such a translucent linear element 58 may be formed by laser engraving a plastic surface, for example. Linear element 58 may alternatively be formed as a through-hole extending entirely through a top surface of inspection tool (which may face an inspector) and a bottom surface of the inspection tool (which may form inspection surface 52 that may be placed on an article 18). In another exemplary configuration, linear element 58 may be formed as a line having a color different than a color of body 50. In one aspect, linear element 58 may include a translucent or opaque linear portion provided within body 50.

A surface feature in body 50 may be formed by one or more circular surface features or circular elements 60. Circular elements 60 may be provided together with linear elements 58. Each circular element 60 may be provided as a shallow groove or recess (e.g., a translucent portion), a through-hole, or a colored circular portion having a color different than a color of body 50, similar to linear element 58. As can be seen in FIG. 4, a plurality of circular elements 60 may be provided together as a group of elements 60. Alternatively, a single circular element 60 may be provided.

Regardless of the form of linear elements 58 and circular elements 60, each may be sized so as to identify a particular physical defect in an article 18. In one aspect, linear element 58 may have a size and shape that corresponds to a first physical defect such as textile snagging that may be present in an article 18 formed as a garment, accessory, or other wearable item. Thus, an inspection standard may be indicated by linear elements 58, as a size of linear element 58 may correspond to an unacceptable size for a textile snag or snag 150 present in article 18 (FIG. 5). In a similar manner, a size of circular element 60 may correspond to another (e.g., second) physical defect in article 18. In one aspect, circular element 60 may have a size and shape that corresponds to a second inspection criterion such as textile pilling (lint) 152 that may be present in articles 18 (FIG. 5). Thus, linear elements 58 and circular elements 60 may correspond to different inspection criteria or different physical defects.

As can be seen in FIG. 4, a plurality of linear elements 58 may be provided. In one aspect, at least two of the linear elements 58 may have different sizes (e.g., lengths). Each differently-sized linear element 58 may correspond to a different inspection standard (e.g., an acceptable size of a snag) that is used in the inspection of a respective inspection area. In another aspect, at least three linear elements 58 have different lengths, as shown in the exemplary configuration of FIG. 4. In another aspect, the number of linear elements 58 with different lengths may be four, five, six, or more. If desired, one or more of the linear elements 58 may have a same size.

In the exemplary configuration of FIG. 4, a plurality of circular elements 60 may be provided. Each of the circular elements 60 for a particular inspection standard may have the same size, but may be arranged in a pattern that facilitates inspection of textile pilling. For example, by providing a grouping of circular elements 60 in which some circular elements 60 are located closer together than other circular elements 60, these elements 60 may facilitate inspection of textile pilling 152 which may occur in a somewhat random manner with textile pills 152 having different sizes. If an inspection standard for pilling varies based on an area of inspection, circular elements 60 may be provided with different sizes for each respective inspection standard.

Body 50 may include an area division indicator 62 that provides a visual or other indication of a plurality of inspection areas for an article 18. As shown in FIG. 4, area division indicator 62 may include a representation of an article divided into a plurality of different zones or areas. Thus, an inspection of article 18 may include evaluating a series of areas or zones (e.g., four zones) of the article having one or more differing inspection standards for a given inspection criteria, the areas being determined by reference to division indicator 62. In one aspect, division indicator 62 may depict or otherwise present different areas of an article (e.g., a garment) such as: a first zone that corresponds to the front of the garment above the waist, a second zone that corresponds to the front of the garment below the waist and the back of the garment above the waist, a third zone that includes the arms and a back of the garment below the waist, and a fourth zone that corresponds to an interior of the garment.

The zones shown in area division indicator 62 are exemplary, and are not necessarily present in all articles. These zones may also differ based on the type of article 18 being inspected. For example, when article 18 is a pair of pants, an inspection tool 14 may include a division indicator 62 that indicates the first zone may be the front of the pants from the waistline to the knee. For some articles 18, such as shorts, T-shirts, etc., fewer than four zones may be present. For other articles 18, such as shoes or suits, five or more zones may be present. When an inspection is performed, as described in detail below, the inspection is performed based on the areas or zones that are actually present in the article.

An inspection standard for determining when an article 18 has failed the inspection may differ based on the zone evaluated and the inspection criterion. For example, while an inspection standard may indicate that any snag 150 may unacceptable in a front of the article 18 (e.g., the first zone), an inspection standard for an area corresponding to a back of article (18) (e.g., the second zone) may indicate that minor snagging is acceptable. Additionally, while no pilling may be acceptable in one or more zones, minor pilling may be acceptable in one or more zones such as zones 3 and 4, for example.

In one aspect, an inspection standard indicator 64 may indicate one or more inspection standards applicable to one or more inspection criteria of articles 18. As shown in FIG. 4, an inspection standard indicated by indicator 64 may correspond to the size of linear elements 58. In another aspect, an inspection standard indicated by indicator 64 may correspond to a size of circular elements 60. The inspection standard corresponding to the size of linear elements 58 and/or the size of circular elements 60 may be based on one or more ASTM (American Society for Testing and Materials) standards, such as an ASTM standard for snagging or pilling.

At an upper portion of body 50, area indicator 66 may be provided to indicate one or more inspection areas. As shown in FIG. 4, for each inspection area indicated by area indicator 66, a respective inspection standard for a plurality of inspection criteria (textile snagging and textile pilling) may be provided. As shown in FIG. 4, some inspection standards for a particular inspection criteria (e.g., pilling) may be the same for multiple areas (e.g., zones 1 and 2, or zones 3 and 4). As also shown in FIG. 4, inspection standards (e.g., an amount of acceptable snagging) may be different for each area (e.g., zones 1, 2, 3, and 4).

As shown in FIG. 4, body 50 may extend within a first length 132 in a width direction and a second length 134 in a length direction. First length 132 of body 50 may be between 7 and 11 inches, for example. In one embodiment, first length 132 may be between 8 and 10 inches. In one embodiment, first length 132 may be approximately 9 inches. Second length 134 may be between 4 and 8 inches. In one embodiment, second length 134 may be between 5 and 7 inches. In one embodiment, second length 134 may be approximately 6 inches. A length 130 of area indicator 66 may be between 0.25 in. and 0.75 in. In one aspect, length 130 may be approximately 0.5 in.

FIG. 5 is a perspective view illustrating an exemplary use of inspection tool 14 in an inspection station 112. As shown in FIG. 5, an inspection performed by an inspector may include placing inspection tool 14 on an article 18 while evaluating article 18 for at least one physical defect. As can be seen in FIG. 5, inspection tool 14 may be placed on article 18 such that an inspection surface 52 located on the bottom surface of body 50 contacts a surface of article 18. In the example of FIG. 5, the inspection tool 14 is placed such that inspection surface 52 touches a back (e.g., zone 2) of article 18. Inspection tool 14 may then be guided along article 18 until one or more of the linear elements 58 or circular elements 60 are approximately aligned with a potential physical defect of article 18. As each of the corners 54 and side edges 56 of inspection tool 14 may be rounded (e.g., by including a convex surface that faces article 18), movement of the inspection tool 14 along article 18 may avoid the creation of any snags, tears, or rips, even when article 18 is formed of a delicate material such as cashmere.

In the exemplary article 18 shown in FIG. 5, potential physical defects may include one or more potential snag defect(s) 150 and potential pilling defects 152. A potential snag defect 150 may be evaluated by placing tool 14 directly on top of the potential snag defect 150. One of the linear elements 58 may be placed in a position that covers a potential snagging defect 150, allowing direct comparison between the size of the linear element 58 and the potential snagging defect 150, as clear body 50 allows for direct viewing of the potential defect 150 through tool 14. Tool 14 may also be placed adjacent to (including above, below, or to the side of) a potential snag defect 150 (as shown in FIG. 5). Any position that allows for a visual comparison of potential snag defect 150 and a linear element 58 may constitute alignment.

To evaluate a potential pilling defect 152, inspection tool 14 may similarly be placed directly on top of one or more potential textile pilling defects 152. One of the circular elements 60 may be placed in a position that covers a potential pilling defect 152, allowing direct comparison between the size of the circular element 60 and the potential pilling defect 152. If desired, tool 14 may also be placed directly on or adjacent to (including above, below, or to the side of) one or more potential pilling defects 152. Any of these positions may provide an alignment between one or more circular element 60 and potential pilling defect 152, in a similar manner as discussed above.

Figure 6:
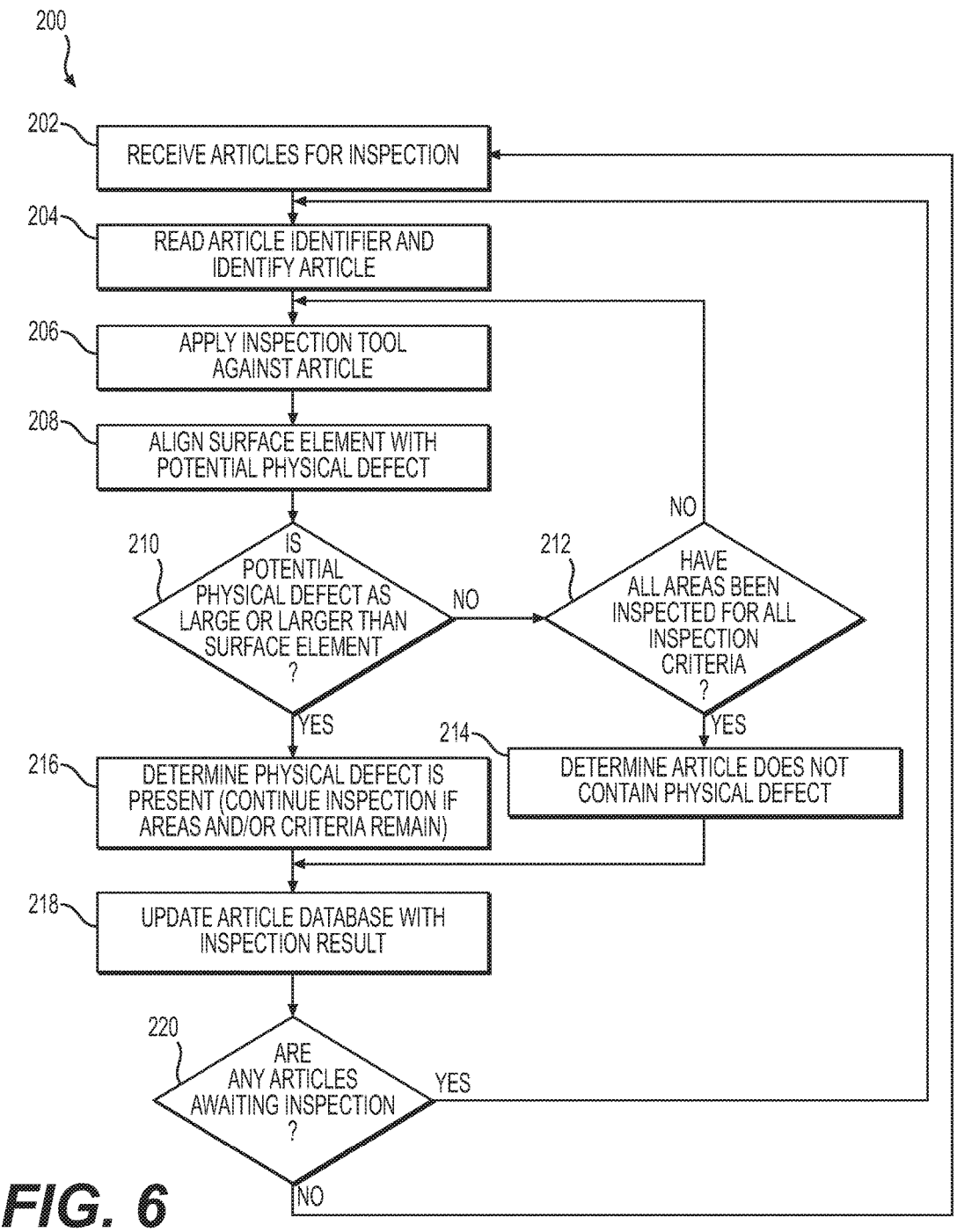
FIG. 6 is a flow diagram illustrating an article inspection process according to an embodiment of the present disclosure.

FIG. 6 is a flowchart of a method 200 for inspecting an article with a defect detection tool 14 according to an embodiment. Method 200 may include computer implementation, e.g., by the operation of inspection processing device 30.

In an initial step 202, articles 18 for inspection may be received at inspection station 112. These articles 18 may be received in a first lane 92 (FIG. 2) of an inspection station 112. Upon being received in inspection station 112, each article 18 may have a unique identifier 22 attached thereto. Step 202 may be performed at any time and/or throughout method 200.

In step 204, reader 28 may read identifier 22 associated with a particular article 18. Reader 28 reads information encoded by identifier 22, for example an alpha-numeric string of characters, and outputs this information to processing device 30. Based on this information, processing device 30 may identify the article 18. For example, the information from reader 28 may uniquely identify article 18. Also, the information from reader 28 may allow processing device 30 to determine article characteristics that are stored locally within memory 36 such as one or more of a source, category, style, color, size, or serial number. Step 204 may also include, based on the identifier 22 querying article tracking system or article database 40. Article database 40 may respond, for example via network 140, with one or more of: article characteristic information, article image information, article inspection history information, or article location information from storage devices 42, 44, 46, and 48.

In a step 206, inspection tool 14 may be placed on or applied to article 18. This may be performed as shown in FIG. 5 by placing an inspection surface 52 on a corresponding surface of article 18, for example. As inspection tool 14 may include a clear body 50, only a small portion of article 18 is obscured by inspection tool 14.

In a step 208, a surface element 58, 60 of inspection tool 14 may be brought into alignment with one or more potential defects such as potential snag defects 150 and/or potential pilling defects 152. As noted above, this alignment may include placing a surface element 58, 60 directly on (e.g., at least partially covering) or adjacent to a potential physical defect. Aligning may include placing a surface element above, below, or to the side of the potential physical defect.

In step 210, a determination may be performed with a surface element 58, 60 of inspection tool 14 aligned with one or more potential physical defects 150, 152. During step 210 a size of potential physical defect 150, 152 is compared to the size of a linear element 58 or a circular element 60, respectively. Thus, step 210 may include evaluating an area of article 18 for the presence of a physical defect. For example, during step 210, a size of linear element 58 may be compared to a size of a potential snag defect 150, as shown in FIG. 5. When the potential physical defect is smaller than the surface element, the determination in step 210 is negative and the process may proceed to step 212. In step 212, a determination is made whether all areas (e.g., zones) of the article 18 have been inspected for all inspection criteria. If the determination is negative, the process may return to step 206 or step 208, as necessary, to perform an evaluation of any remaining criteria. Thus, different areas of article 18 may be evaluated for different inspection standards corresponding to the same criterion. A first area of article 18 (e.g., zone 2) may have a first potential snag defect 150 that is compared to a first linear element 58. A second area of article 18 (e.g., zone 3) may include a second potential snag defect 150 that is compared to a second linear element 58 that has a size different from the first linear element 58. A physical defect sufficient for article 18 to fail inspection may be determined to be present in article 18 when either the first potential snag defect 150 is larger than the first linear element 58 or the second potential snag defect 150 is larger than the second linear element 58. Such a determination is not limited to two areas of an article 18, or to two inspection standards (e.g., two sizes of linear element 58). In the example of snagging, four areas of article 18 may be evaluated for four or more different inspection standards.

In one aspect, if the determination in step 212 is negative and the inspection tool is no longer needed, (for example when the article 18 requires inspection for one or more of the presence of a stain, color bleeding, tearing, broken stitching, odor, dirt, wrinkling, shrinkage, wear, color fading, missing or broken hardware, or missing or broken embellishments), the evaluation may proceed with be by evaluating each of the remaining inspection criterion.

When the determination in step 212 is affirmative, each area of article 18 has been inspected and all inspection criteria have been evaluated. Thus, the article 18 does not contain a physical defect such as snagging or pilling.

In step 214, a determination may be made that the article 18 does not contain a physical defect. This determination may include entering a result of the inspection (e.g., pass) into inspection processing device 30.

Returning to step 210, when the potential physical defect is as large, or larger, than the corresponding surface element 58, 60, the process may proceed to step 216 in which a physical defect is determined to be present. Step 216 may include proceeding with a complete inspection of all areas and for all inspection criteria. Thus, if the physical defect is reparable, it may be unnecessary to return the article 18 to inspection station 112, and the article 18 may be transferred to transfer station 114 following repair. Step 216 may include entering a result of the inspection (e.g., fail) into inspection processing device 30.

In a step 218, article tracking system or article database 40, including inspection history storage 46, may be updated with the result of the inspection for article 18 that was determined in step 214 or 216. This update may be based on the inspection performed with inspection tool 14 and the identification of article 18 based on article identifier 22. Thus, when step 218 is reached based on a passed inspection (via step 214), inspection history storage 46 may be updated by inspection processing device 30 to reflect the passed inspection. Similarly, when step 218 is reached based on a failed inspection (via step 216), inspection history storage 46 may be updated by inspection processing device 30 to reflect the failed inspection. This may include updating inspection history storage 46 with a cause of the failure (e.g., snagging and/or pilling) determined with the use of tool 14.

In step 220, it may be determined if more articles 18 are present in inspection area 112 and are awaiting inspection. If the determination in step 220 is affirmative, the process may proceed to step 204 and these articles 18 may be inspected. When the determination in step 220 is negative, step 202 may be again performed to continue the inspection process with additional articles 18.

Figure 7:
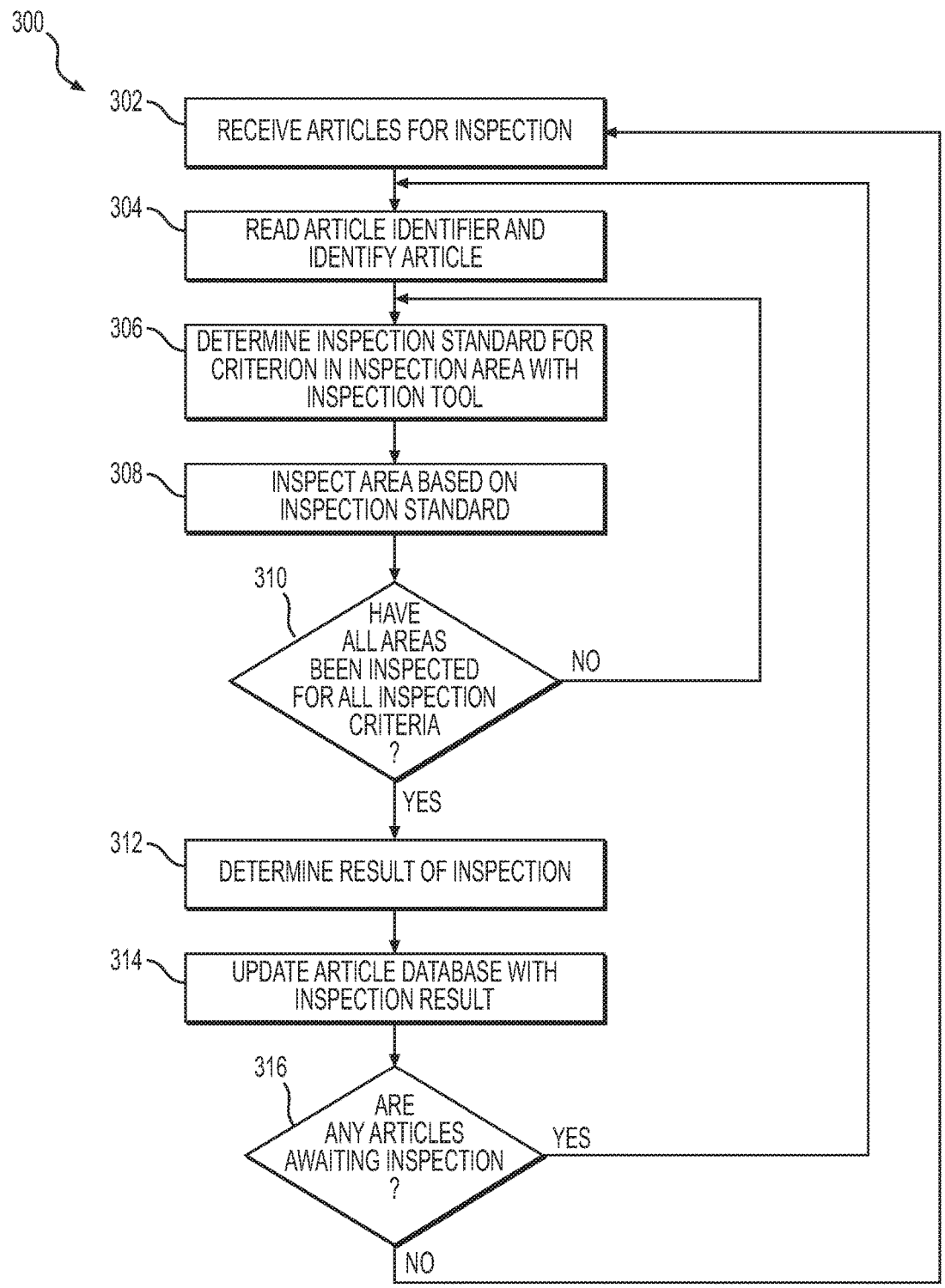
FIG. 7 is a flow diagram illustrating an article inspection process according to an embodiment of the present disclosure.

FIG. 7 is a flowchart of a method 300 for detecting a defect in an article 18. In one aspect, method 300 may be a method that is at least partially computer-implemented, for example with the use of inspection processing device 30.

In an initial step 302 of method 300, one or more articles 18 may be received at an inspection station 112. This may be performed in the same manner as step 202 described above. Similarly, in a step 304 may be performed in the same manner as step 304 for reading an article identifier 22 and identifying the article 18 based on the article identifier 22.

In a step 306, an inspection standard for an inspection criterion (e.g., snagging and/or pilling) in an inspection area (e.g., zone) may be determined. For example, with reference to FIG. 4, area division indicator 62 that may be used to determine the location and/or boundaries of one or more areas of an article 18. An inspection standard indicator 64 provided in body 50 with area division indicator 62 may be used to determine an inspection standard for each area (e.g., no snagging, snag less than 0.25 in. may be acceptable, snag less than 0.5 in. may be acceptable, snag less than 1.0 in. may be acceptable, etc.).

Step 306 may include determining an inspection standard based on area indicator 66 and one or more of linear elements 58 or circular elements 60. When an inspection standard in an area (e.g., zone 1) does not permit a defect of any size, this may be indicated in an area of body 50 adjacent to area indicator 66 to allow a determination of the inspection standard in the corresponding area. The inspection standard for each area may also be determined visually based on the size of one or more linear elements 58 and/or one or more circular elements 60.

In a step 308 that may follow completion of step 306, an inspection may be performed by evaluating an article 18 based on the criterion determined in step 306. This may be performed, for example, by applying an inspection tool 14 to an article 18 (see step 206 as described above), aligning a surface element of inspection 14 with one or more potential defects (see step 208 as described above), and determining whether a physical defect is as large or larger than the surface element (see step 210 as described above).

The surface element (e.g., one of the linear elements 58) compared to the potential physical defect may have a size that reflects the inspection standard determined in step 306. For example, when an area (e.g., zone 2) of an article 18 is evaluated, as shown in FIG. 5, a surface element corresponding to this area (zone 2) may be aligned with a potential physical defect. In the example illustrated in FIG. 5, the area under inspection may be considered zone 2, and a linear element 58 corresponding to zone 2 (as may be indicated by area indicator 66) may be aligned with a potential snag defect 150. In such an example, the physical defect may be determined to exist when the size of the potential snag defect 150 is larger than the linear element 58 that reflects the appropriate inspection standard (e.g., the linear element 58 for zone 2).

In a step 310 that may follow step 308, a determination may be made whether all areas (e.g., zones) of the article 18 being inspected have been inspected for all inspection criteria. Step 310 may be performed in the same manner as step 212.

In a step 312, a result of the inspection may be determined once all areas of an article 18 have been inspected for all inspection criteria. Step 312 may include determining that article 18 passed inspection when no physical defects were present. Step 312 may involve inspecting for quality criteria including, but not limited to: staining, color bleeding, tearing, broken stitching, odor, dirt, wrinkling, shrinkage, wear, color fading, missing or broken hardware, or missing or broken embellishments.

In a step 314, article inspection tracking system or database 40 may be updated with the inspection result. In one aspect, this update may be performed in the same manner described above with respect to step 218, by providing an update to inspection history storage 46 with inspection processing device 30.

Step 316 may include determining if more articles are awaiting inspection in inspection area 112, as described above with respect to step 220. If this determination is affirmative, the process may return to step 304. When the determination in step 316 is negative, the process may return to step 302. Thus, a plurality of articles 18 may be inspected using tool 14.

By performing an inspection with the systems and methods described herein, inspections may be performed based on objective criteria. Additionally, inspections may be consistently performed, even when inspection criteria are different for different areas of an article being evaluated in the inspection. In one aspect, the use of an inspection tool 14 may allow for the determination of a standard for inspecting one or more areas of the article. Additionally, one or more surface features may provide a physical representation of one or more inspection criteria. Thus, the exemplary systems and methods may improve the speed, quality, and accuracy of article inspections.

What is claimed is:

1. A method of inspecting an article with a defect detection tool, comprising:
    receiving one or more articles at an inspection station; and
    inspecting one of the received one or more articles at the inspection station by evaluating the article for at least one physical defect with the defect detection tool, the defect detection tool comprising:
        a clear body comprising a surface element sized to correspond to the at least one physical defect in the article, the surface element including at least one of a linear element or a circular element, the surface element formed as a depression, a through-hole, or a portion of the body having a color different than the clear body, and
        an inspection surface configured to contact a surface of the article,
    wherein evaluating the article for at least one physical defect with the defect detection tool comprises:
        applying the defect detection tool against the article to align the surface element with a potential physical defect in the surface of the article, and
        determining that the at least one physical defect is present based on a size of the potential physical defect, wherein the size of the potential physical defect is equal to or larger than a size of the linear element or a size of the circular element.

2. The method of claim 1, wherein the article is a wearable item.

3. The method of claim 2, wherein the wearable item is a garment.

4. The method of claim 2, wherein the surface element includes the circular element, the circular element formed as a depression, a through-hole, or a portion of the body having a color different than the clear body.

5. The method of claim 2, wherein the surface element includes the circular element, and the method further includes comparing a size of a textile pill on the wearable item to the size of the circular element.

6. The method of claim 2, wherein the surface element includes the linear element, and the method further includes comparing a size of a potential snag defect on the wearable item to the size of the linear element.

7. The method of claim 6, further including:
    comparing a first potential snag defect in a first area of the article to a first linear element of a plurality of linear elements;
    comparing a second potential snag defect in a second area of the article to a second linear element of the plurality of linear elements, the first linear element and the second linear element having different sizes; and determining that the at least one physical defect is present based on a size of at least one of the first potential snag defect or the second potential snag defect, wherein the size of the first potential snag defect is equal to or larger than the first linear element or the size of the second potential snag defect is equal to or larger than the second linear element.

8. The method of claim 1, wherein the surface element includes the circular element and the linear element, and evaluating the article includes comparing a size of a potential pilling defect on the wearable item to the size of the circular element and comparing a size of a potential snag defect on the wearable item to the size of the linear element.

9. The method of claim 8, further including, based on a presence of the at least one physical defect in the article, determining that the article failed the inspection and recording a failed inspection with an inspection processor.

10. An inspection defect detection tool for detecting at least one physical defect in an article, comprising:
a clear body having a surface element sized to correspond to the at least one physical defect in the article, the surface element including at least one of a linear element or a circular element, the surface element formed as a depression, a through-hole, or a portion of the inspection surface having a color different than the clear body; and
an inspection surface formed on the clear body, the inspection surface configured to contact a surface of the article such that the surface element is approximately aligned with a potential physical defect in the article.

11. The inspection defect tool according to claim 10, wherein a plurality of surface elements are provided, the linear element forms a first surface element and a circular through-hole is provided as a second surface element.

12. The inspection defect tool according to claim 10, wherein a plurality of linear elements are provided, the linear elements having different lengths corresponding to respective areas of the article.

13. The inspection defect tool according to claim 10, wherein the article is a wearable item.

14. The inspection defect tool according to claim 13, wherein the wearable item is a garment.

15. The inspection defect tool according to claim 13, wherein the surface element includes the circular element, and wherein a size of the circular element is compared to a size of a textile pill on the wearable item.

16. The inspection defect tool according to claim 13, wherein the surface element includes the linear element, and wherein a size of the linear element is compared to a size of a potential snag defect on the wearable item.

17. The inspection defect tool according to claim 13, wherein the surface element includes the circular element and the linear element, and wherein a size of the circular element is compared to a size of a potential pilling defect on the wearable item and a size of the linear element is compared to a potential snag defect on the wearable item.

* * * * *